Dec. 13, 1960 E. S. BOERNER Plant Pat. 1,999
ROSE PLANT
Filed March 1, 1960
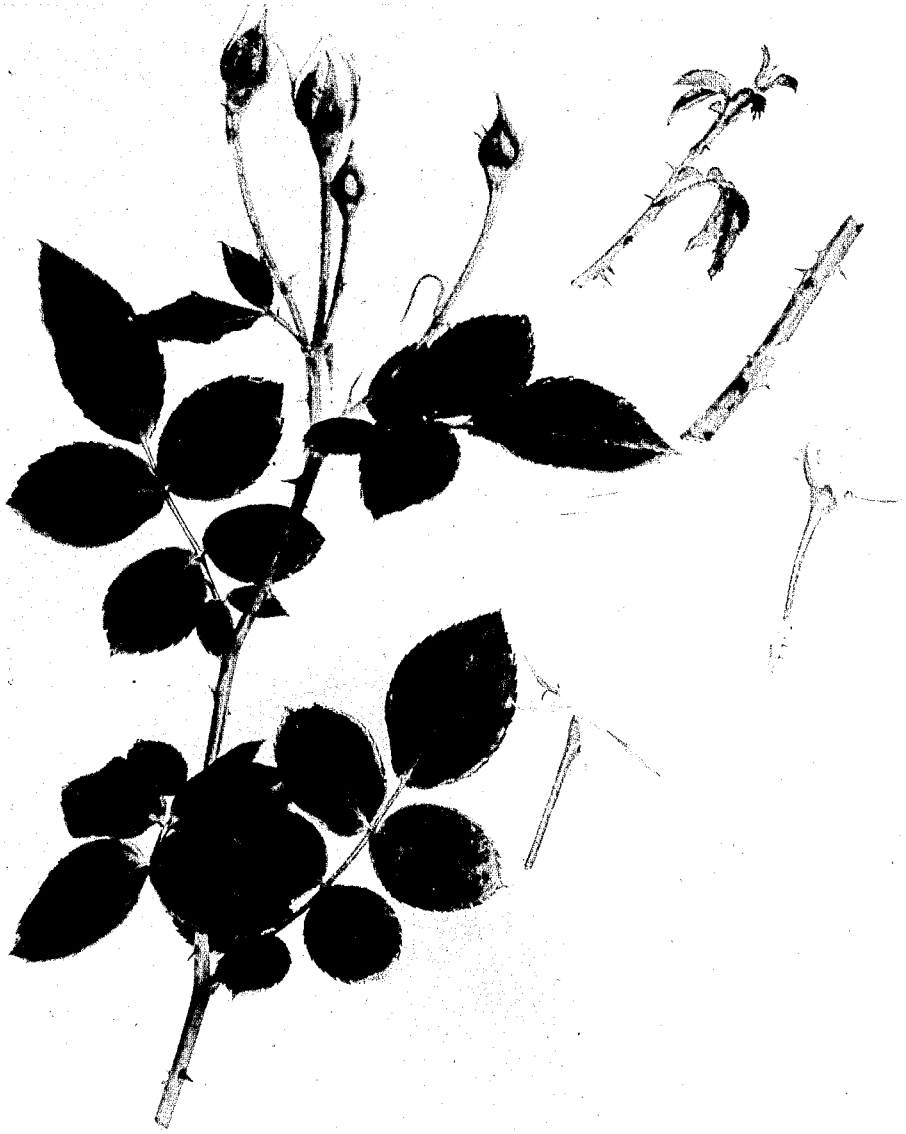
Inventor.
E. S. Boerner
By: Robbins & Cobb
attorneys.

United States Patent Office

Plant Pat. 1,999
Patented Dec. 13, 1960

1,999

ROSE PLANT

Eugene S. Boerner, Newark, N.Y., assignor to Jackson & Perkins Company, Newark, N.Y., a corporation of New York Filed Mar. 1, 1960, Ser. No. 12,241

1 Claim. (Cl. 47—61)

The present invention relates to a new and distinct variety of rose plant of the floribunda class, which was originated by me by crossing the variety "Goldilocks" (Plant Patent No. 672) with the variety "Fashion" (Plant Patent No. 789).

The primary objective of this breeding was to produce a new rose variety of the floribunda class which combines the hardiness, form and blooming value of the parent variety "Goldilocks" with a flower color different from that of this parent. This objective was fully achieved, along with other desirable improvements, as evidenced by the following unique combination of characteristics which are outstanding in the new variety and which distinguish it from its parents, as well as from all other varieties of which I am aware:

(1) A compact and upright plant habit;

(2) Good hardiness, as inherited from the hardy variety "Goldilocks" and the very hardy variety "Fashion";

(3) Foliage which is usually composed of seven leaflets;

(4) A cupped flower shape;

(5) A continuous blooming habit throughout the summer; and (6) A distinctive general color tonality of the flowers corresponding to Marguerite Yellow, lightly overcast with Eosine Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Goldilocks."
*Pollen parent.*—"Fashion."

Classification:
*Botanic.*—"Floribunda."
*Commercial.*—"Floribunda."

*Flower*

(Observations made from specimens grown out-doors at Newark, New York, near the middle of the afternoon during the middle part of the month of September.)

Blooming habit: Recurrent—continuous.

Bud:
*Size.*—Medium.
*Form.*—Ovoid; is not affected by wet or hot weather.
*Color.*—When sepals first divide—Chartreuse Yellow, Plate 31. When sepals begin to unfurl—lower half of petals Pinard Yellow, Plate 4, with upper half of petals lightly overcast with Light Jasper Red, Plate 13. When half-blown: inside of petals—Eosine Pink, Plate 1, lightly overcast with Marguerite Yellow, Plate 30; reverse of petals—Ivory Yellow, Plate 30, with outer edge of petals lightly overcast with Chatenay Pink, Plate 13.

*Sepals.*—Branched; curl back when petals begin to unfurl. Color: inside—Pale Glaucous Green, Plate 33; outside—Light Bice Green, Plate 17.
*Calyx.*—Color—Light Bice Green, Plate 17. Shape—funnel. Size—small. Aspect—smooth. Odor when rubbed—none.
*Peduncle.*—Length — medium. Aspect — smooth. Strength—erect; slender. Color—Biscay Green, Plate 17.
*Opening.*—Opens up well; is not affected by adverse weather conditions.

Bloom:
*Size.*—Medium. Average size when fully expanded—3 inches.
*Borne.*—Singly, several together, and also in pyramidal clusters.
*Stems.*—Medium length; strong.
*Form (when first open).*—Cupped. Permanence—flattens and outer petals curl back slightly.
*Petalage.*—Double (full but open center). Number of petals under normal conditions—30.
*Color.*—Center of flower—Baryta Yellow, Plate 4, lightly overcast with Eosine Pink, Plate 1. Outer petals—Ivory Yellow, Plate 30, lightly overcast with Eosine Pink, Plate 1. Base of petals (aiglet) Picric Yellow, Plate 4. Inside of petals—Marguerite Yellow, Plate 30, lightly overcast with Eosine Pink, Plate 1. Reverse of petals—Ivory Yellow, Plate 30, with the upper half of the petals lightly overcast with La France Pink, Plate 1. General tonality from a distance—Marguerite Yellow, Plate 30, lightly overcast with Eosine Pink, Plate 1.
*Discoloration.*—General tonality at end of first day—Marguerite Yellow, Plate 30, lightly overcast with Eosine Pink, Plate 1. Second day—Marguerite Yellow, Plate 30, lightly overcast with Eosine Pink, Plate 1. Third day—Ivory Yellow, Plate 30, lightly overcast with Eosine Pink, Plate 1.

Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Small; many; regularly arranged around styles. Color—Deep Chrome, Plate 3.
Stamens, filaments (threads): Medium length. Color—Picric Yellow, Plate 4.
Pollen: Color—Pale Orange-Yellow, Plate 3.
Styles: Columnar; uneven length; medium length; thin.
Stigmas: Color—Barium Yellow, Plate 16.
Ovaries: All enclosed in calyx.

Hips: None.
Seeds: None.

*Plant*

Form: Bush.
Growth: Vigorous; upright; upright; compact; hardy.
Foliage: Compound of 3 to 7 leaflets, but usually 7.
*Size.*—Medium.
*Quantity.*—Normal.
*Color.*—New foliage: upper side—Spinach Green, Plate 5, lightly overcast with Oxblood Red, Plate 1; under side—Oxblood Red, Plate 1, with center of leaf Oil Green, Plate 5. Old foliage: upper side—Dark Green, Plate 18; under side—Light Elm Green, Plate 17.
*Shape.*—Oval pointed.
*Texture.* — Upper side — leathery. Under side — smooth.
*Ribs and veins.*—Ordinary.
*Edge.*—Serrated (saw-toothed).
*Serration.*—Single; small.
*Leaf stem.*—Color—Lincoln Green, Plate 41. Under side—prickly.
*Stipules.*—Short; smooth.

Wood:
*New wood.*—Color—Parrot Green, Plate 6. Bark—smooth.
*Old wood.*—Color—Cress Green, Plate 31. Bark—smooth.
Thorns:
*Thorns.*—Quantity: on main stalks from base—ordinary; on laterals from stalk—ordinary. Form—narrow base; medium length; straight. Color (when young)—Eugenia Red, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant, of the floribunda class, substantially as herein shown and described, characterized particularly as to novelty by the unique combination of a compact and upright habit of growth, good hardiness, foliage usually composed of seven leaflets, a cupped flower shape, a continuous blooming habit throughout the summer, and a distinctive general color tonality of the flowers corresponding to Marguerite Yellow, lightly overcast with Eosine Pink.

No references cited.